United States Patent
Dell et al.

[11] Patent Number: 5,806,943
[45] Date of Patent: Sep. 15, 1998

[54] MOBILE WORKSTATION

[75] Inventors: John J. Dell, Upper St. Clair; H. Mark Hall, Pittsburgh, both of Pa.

[73] Assignee: Sculptor Developmental Technologies, Inc., Pittsburgh, Pa.

[21] Appl. No.: 707,905

[22] Filed: Sep. 12, 1996

[51] Int. Cl.$^6$ .................................................. A47B 81/00
[52] U.S. Cl. ........................ 312/223.3; 108/50; 108/147; 312/197; 312/239; 312/208.2; 248/161
[58] Field of Search ................. 312/223.3, 196, 312/197, 208.1, 208.2, 237, 239; 108/147, 50, 25; 248/161, 404

[56] References Cited

U.S. PATENT DOCUMENTS

| | | |
|---|---|---|
| D. 357,781 | 4/1995 | Crinion . |
| 3,891,270 | 6/1975 | Crossman et al. ................... 248/404 X |
| 4,094,255 | 6/1978 | Zaccaria ..................................... 108/25 |
| 4,428,631 | 1/1984 | Cope et al. ........................... 312/223.3 |
| 4,828,208 | 5/1989 | Peterson et al. . |
| 4,922,836 | 5/1990 | Damico . |
| 5,011,227 | 4/1991 | van Hekken et al. . |
| 5,044,284 | 9/1991 | Gross ................................ 312/223.3 X |
| 5,078,351 | 1/1992 | Gualtieri ................................... 248/161 |
| 5,174,223 | 12/1992 | Nagy et al. ............................... 108/50 |
| 5,287,815 | 2/1994 | Gross ................................ 312/208.1 X |
| 5,289,782 | 3/1994 | Rizzi et al. . |
| 5,386,355 | 1/1995 | Acks ........................................ 362/267 |
| 5,443,017 | 8/1995 | Wacker et al. ...................... 108/147 X |
| 5,450,800 | 9/1995 | Leonard ........................... 312/223.3 X |

*Primary Examiner*—Peter M. Cuomo
*Assistant Examiner*—Stephen Vu
*Attorney, Agent, or Firm*—Buchanan Ingersoll, P.C.

[57] ABSTRACT

A mobile workstation capable of supporting various types of electrical or diagnostic equipment for use primarily in the health care environment comprising a work surface supported by a pedestal and a base. The base includes casters for easy portability of the workstation. The workstation further includes a height adjustment mechanism and a counterbalance. The counterbalance may be supported from the underside of the top of the work surface of the workstation for counterbalancing the weight of the equipment that may be carried on the work surface so as to provide versatility when adjusting the height of the workstation from a seated position to a standing position with minimal effort from the user.

7 Claims, 6 Drawing Sheets

2

MOBILE WORKSTATION

BACKGROUND OF THE INVENTION

1. Field of the Invention

This invention relates to a mobile workstation and more particularly to a mobile workstation having a height adjustment capability wherein the height of the workstation can be adjusted from a seated position to a standing position therefore providing ease and versatility of use in hospital and other health related industries.

2. Description of the Related Art

The healthcare industries and hospitals in particular have become increasingly aware of the need for technology and various diagnostic procedures that are required to be performed in hospital rooms and as part of out-patient services. There exists a need for a workstation that is easily portable and height adjustable that can be used by a variety of hospital and health related personnel in either a standing position or a seated position.

Mobile workstations are well-known in the art. An example of such is United States Design Patent No. 357,781 to Crinion relating to a cabinet-like structure having casters that may be easily transported from one location to another. Furthermore, there is known in the art various height adjustable articles including tables and chairs, such as U.S. Pat. No. 4,922,836 to Damico and U.S. Pat. No. 5,011,227 to Van Hekken et al. However, the items known in the art are either large or cumbersome thus making it difficult to transport from one room or floor to another.

With the increased reliance on technology, there exists a need for a workstation that can support various sizes and weights of equipment including computers, lap/top computers and other diagnostic equipment for use in the hospital and health related industry. Moreover, there exists a need for a portable workstation that can support this equipment and also be easily transported from room to room and from floor to floor. Finally, there exists a need for a workstation that includes height adjustment capabilities so that a user may easily sit or stand while performing various procedures, therefore providing ease and versatility of use for a variety of personnel.

SUMMARY OF THE INVENTION

A mobile workstation is disclosed comprising a work surface which includes a top surface and a bottom surface, a pedestal for supporting the work surface and a height adjustment mechanism that is housed inside the pedestal. The pedestal also includes a base which may have casters or rollers for easy portability of the workstation. Furthermore, the workstation may include a counterbalance means for counterbalancing the weight of various equipment that may be carried on the work surface.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings, wherein:

DESCRIPTION OF THE PREFERRED EMBODIMENT

The height adjustable workstation described herein is for use primarily by hospital and other health related personnel and includes a work surface supported by a pedestal or leg and a base. The base includes casters which make the workstation easily portable from room to room and from floor to floor. The workstation is capable of supporting a lap/top computer or other various types of electrical or diagnostic equipment. The work station also includes a counterbalance means which may be supported from the underside of the top of the work surface of the workstation and is used to counterbalance the weight that may be carried by the work surface so that when the height of the workstation is adjusted the counterbalance means provides easy movement of the workstation with minimal effort from the user.

Figure 1:
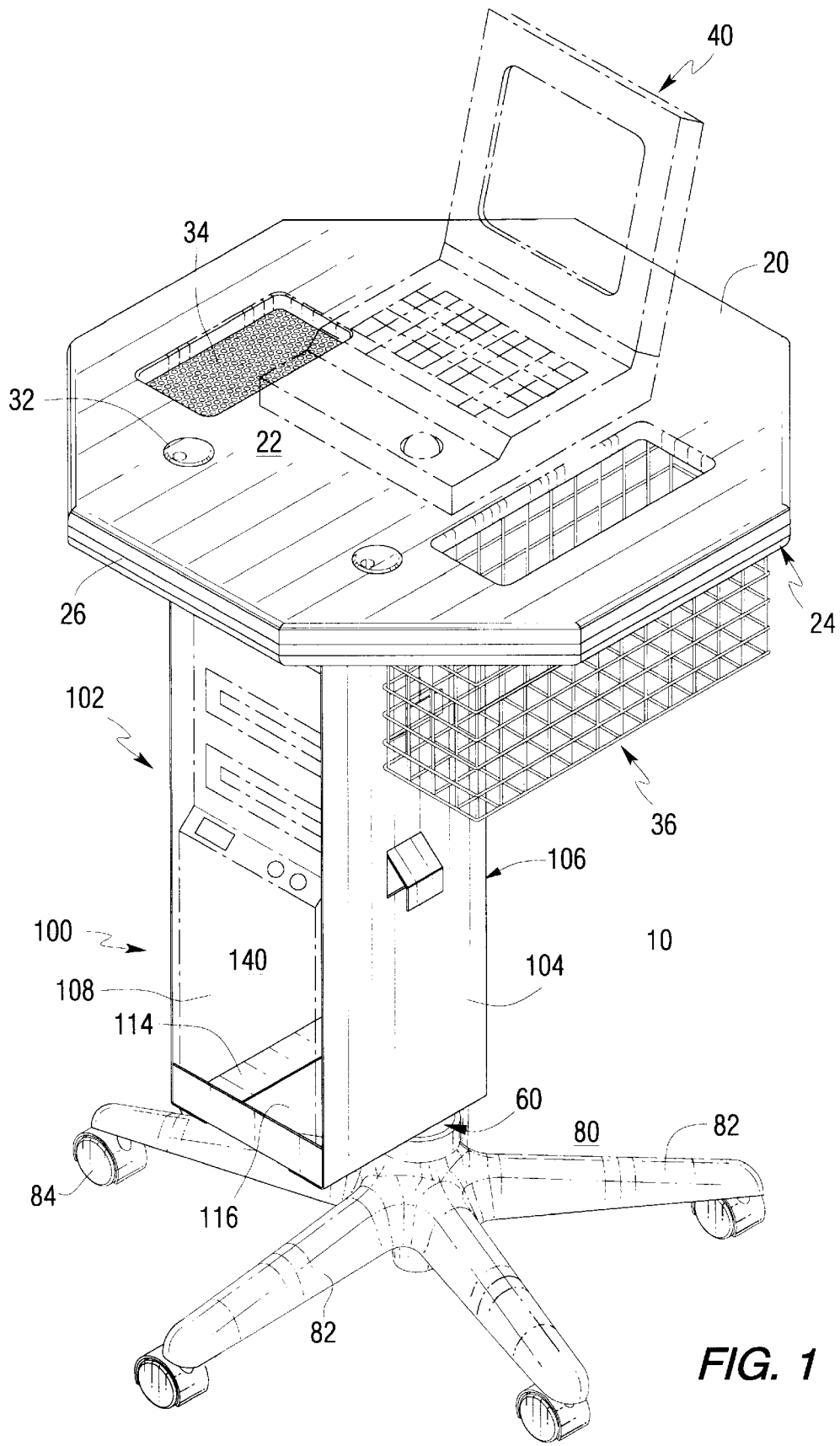
FIG. 1 is a perspective view of the workstation of this invention.
Figure 2:
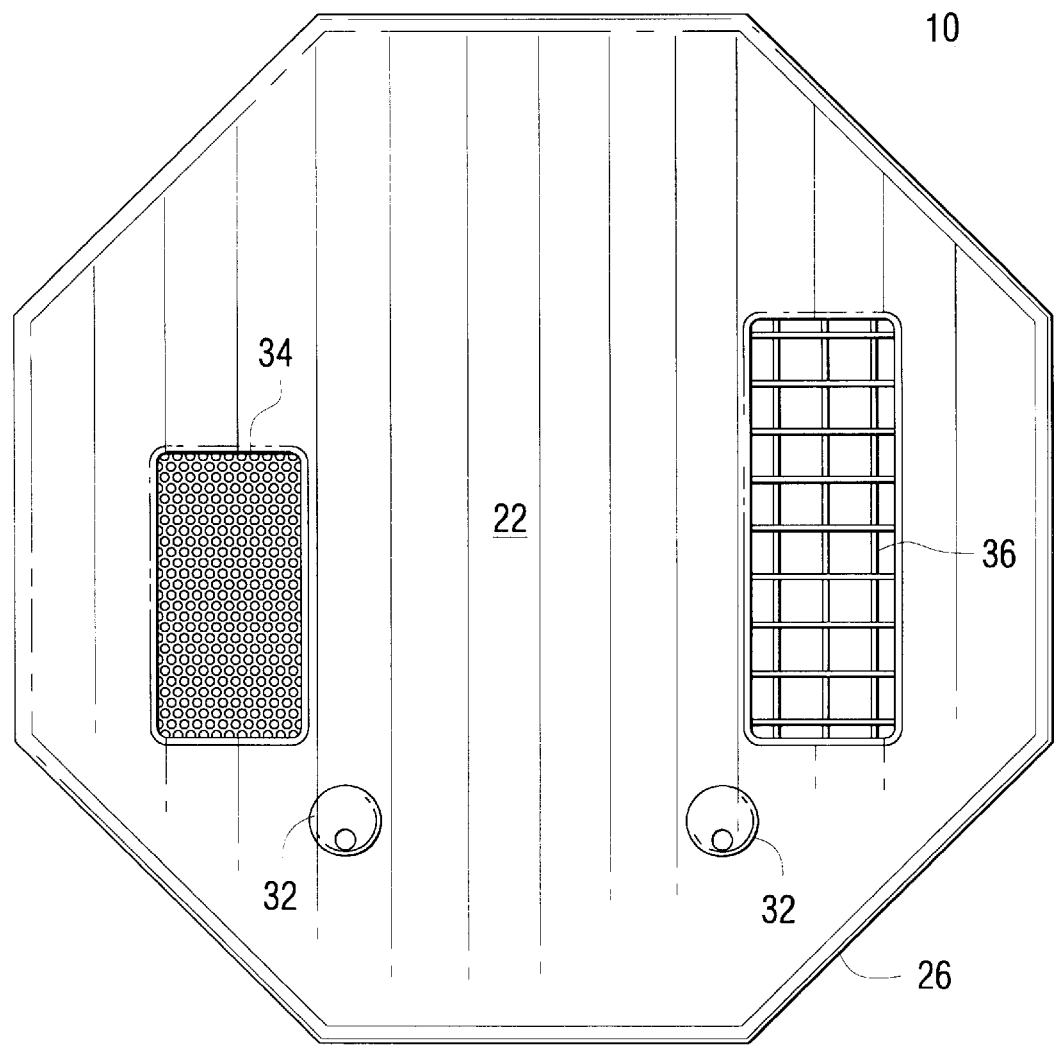
FIG. 2 is a top plan view of the workstation.
Figure 3:
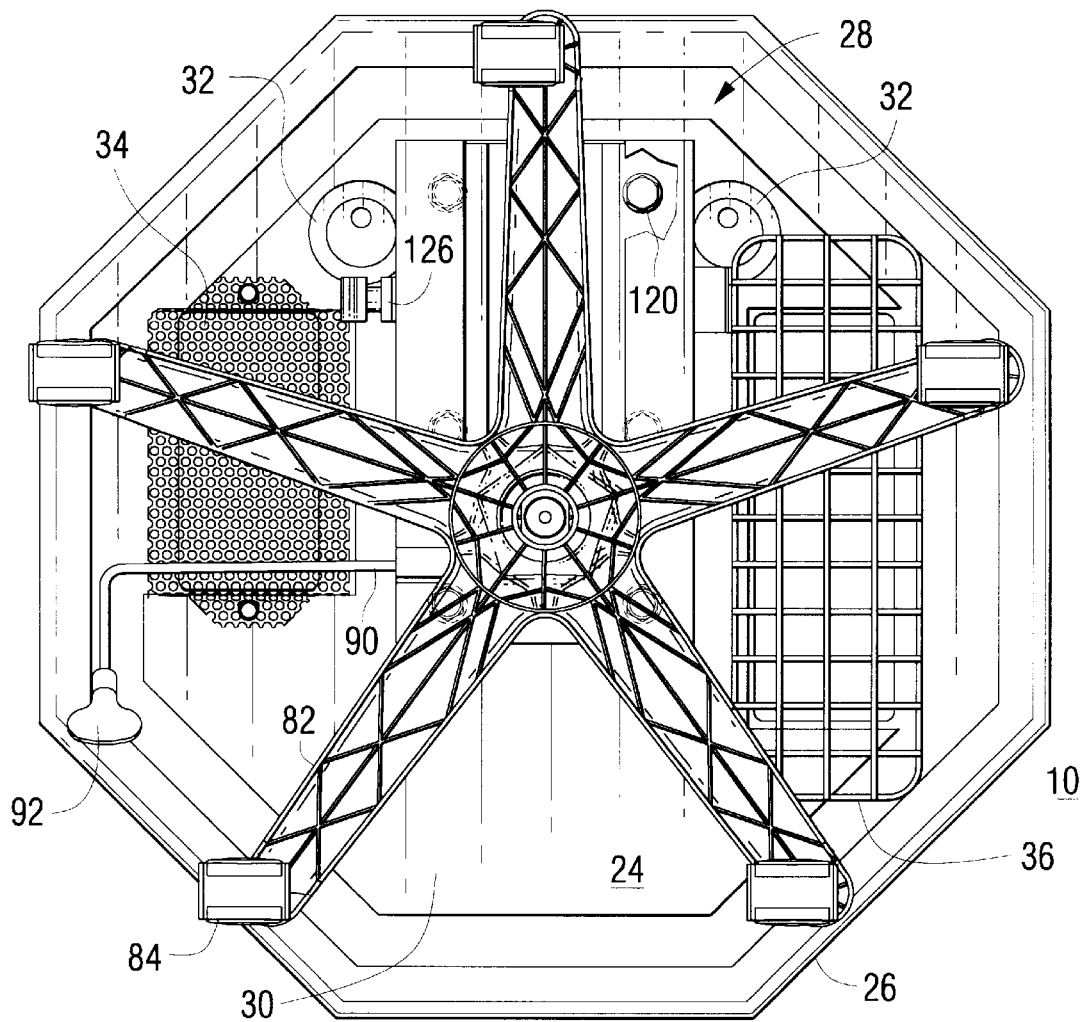
FIG. 3 is a bottom plan view of the workstation.
Figure 4:
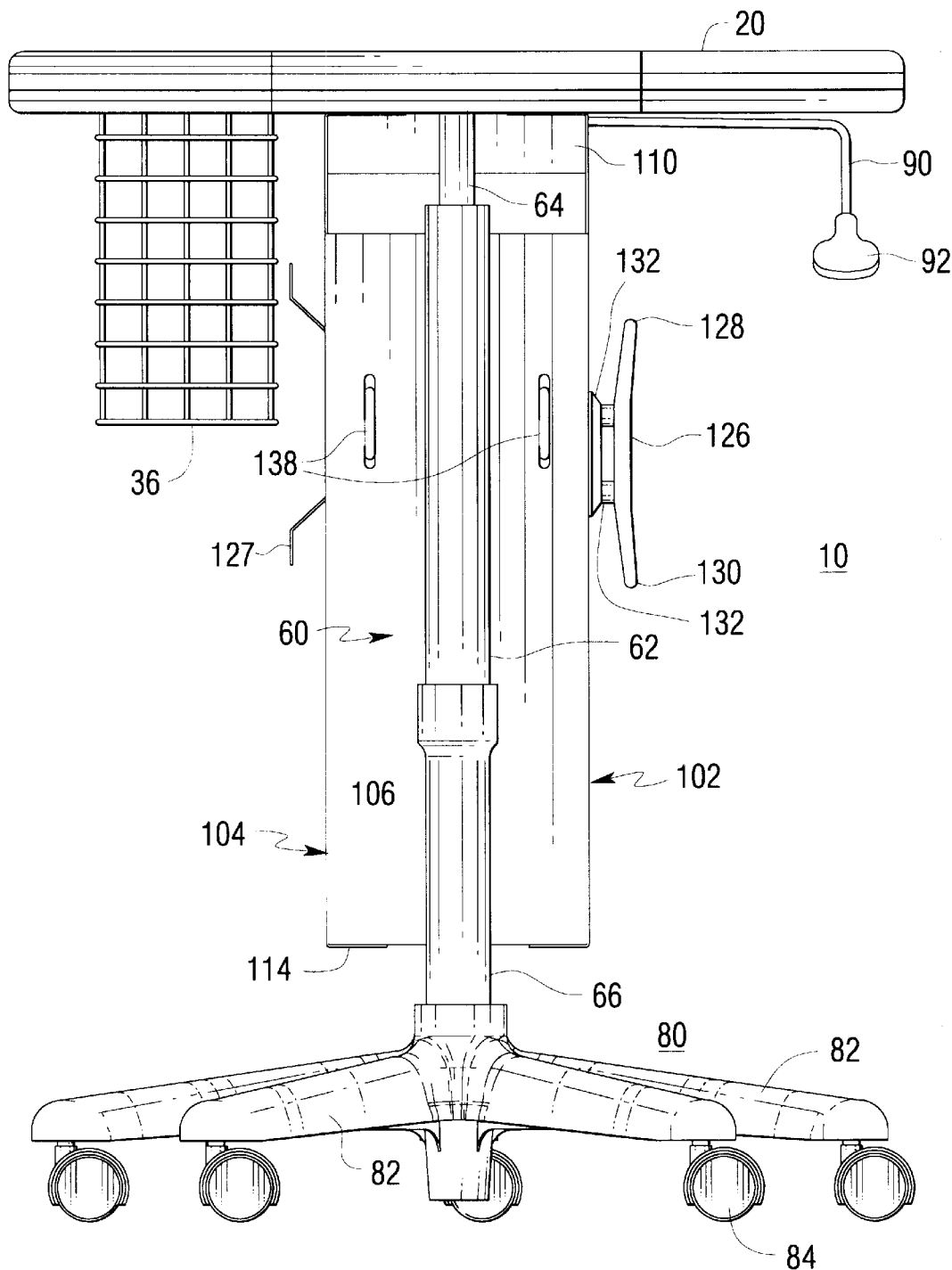
FIG. 4 is a real elevational view of the workstation.
Figure 5:
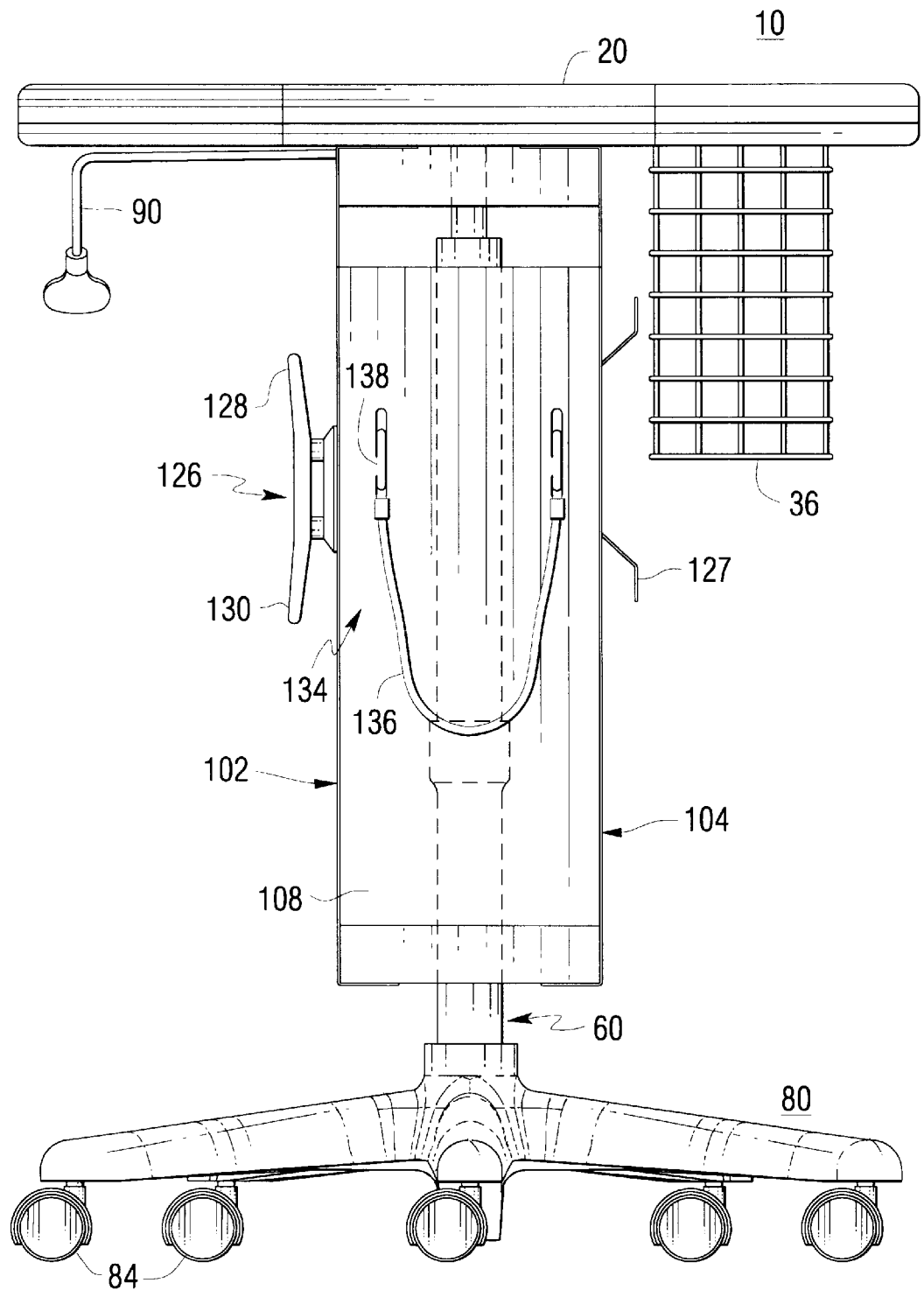
FIG. 5 is a front elevational view of the workstation.

Referring now in detail to the drawings wherein like reference characters represent like parts throughout several views, there is illustrated in FIG. 1 a workstation 10. Workstation 10 includes a work surface 20 supported by a pedestal or leg 60 and a base 80. Work surface 20 includes a top surface 22 and a bottom surface 24. The work surface is preferably an eight sided octagonal shape with eight side edges 26 along the outer perimeter of the work surface. Bottom surface 24 of the work surface, better illustrated in FIG. 3, includes a recess or ledge 28 which surrounds the perimeter of the bottom surface of the workstation and provides a finger hold or grip for ease of movement of the workstation. Bottom surface 24 of the work surface 20 also includes a bottom plate 30 which is positioned toward the center of bottom surface 24 of work surface 20. The top surface of the work surface may be constructed of any type of material, for example, a smooth surface polymer, by casting, pouring or molding and may include several openings which may be used for a variety of functions. These openings can include grommets 32 which can be used to route wires or locking equipment in which to lock a lap/top computer (40 shown in phantom) or other equipment that may be carried on top of the work surface. Openings may also include spaces for baskets or bins 34, 36. Baskets 34, 36 can include a smaller basket 34 which may be constructed of wire mesh and may have an approximate depth of 1 and ½ inches. Smaller basket 34 can be used to hold pencils, pens or other small items. Basket 36 is a larger basket having dimensions of approximately 12 inches in depth, 4 inches in length and 1 inch in width. Basket 36 may also be constructed of wire mesh and may be used to hold charts or other types of diagnostic equipment.

Pedestal 60 includes a leg which is attached to bottom plate 30 of bottom surface of work surface 20. The pedestal includes an upper inner tube 62 which houses a height adjustment mechanism, typically a piston and cylinder 64. Piston and cylinder 64 may be of the standard variety 70 pound, ten inch stroke. Piston and cylinder 64 is mounted inside inner tube 62. Pedestal 60 also includes a lower outer tube 66 which culminates in a base 80. Base 80 is preferably made of plastic material and includes a five star spoke design. Spokes 82 radiate out from the bottom of the base to provide support and distribute weight that may be carried on the work surface. Base 80 also includes casters 84 for ease of portability of workstation 10. A release mechanism 90 is mounted to bottom surface 24 of a work surface 22 and operates piston and cylinder 64. Release mechanism 90 includes a lever 92 which is easily actuated by the user to raise and lower the work surface of workstation.

Workstation 10 further includes a counterbalance means 100 which comprises a compartment which may be constructed of sixteen gauge carbon steel having a black powder coat finish. Compartment 100 may be a three-sided, C-shaped container including sides 102, 104, rear side 106 and open side 108. Compartment 100 also includes an upper ledge 110 including openings at 112 and a bottom ledge 114, including an opening 116. The configuration of compartment 100 is C-shaped with the upper ledge 110 and bottom ledge 114 also including a C-shaped design. Compartment 100 is mounted to bottom plate 30 of bottom surface 24 of the work surface by attachment means such as screws or bolts 120 and the compartment is therefore suspended from the bottom surface of the work surface. Compartment 100 also includes a cleat 126 preferably mounted to side 102. Side 102 is the opposite side from side 104 which is adjacent basket 36. An additional cleat 127 may be mounted to side 104. Cleat 126 includes an upper prong 128 and lower prong 130 with side arms 132 attached to side 102. Cleat 126 is used to wrap and store electrical cords or the like when the workstation is in use so as not to interfere with the movement of the workstation. Compartment 100 also includes securement means 134 which includes an elastic strap 136 and hooks 138 which are attached to slots on rear side 106. Finally, the counterbalance means may also include a ballast 140 which may be in the form of an uninterruptable power supply (shown in phantom) which may be inserted into compartment 100 through open side 108, supported by bottom ledge 114, and removably secured by securement means 134. Power supply 140 can also include an electrical cord which can depend through opening 116 in bottom ledge 114 and can be wrapped around cleat 126 so as to prevent the electrical cord from interfering with the movement of the workstation.

Figure 6:
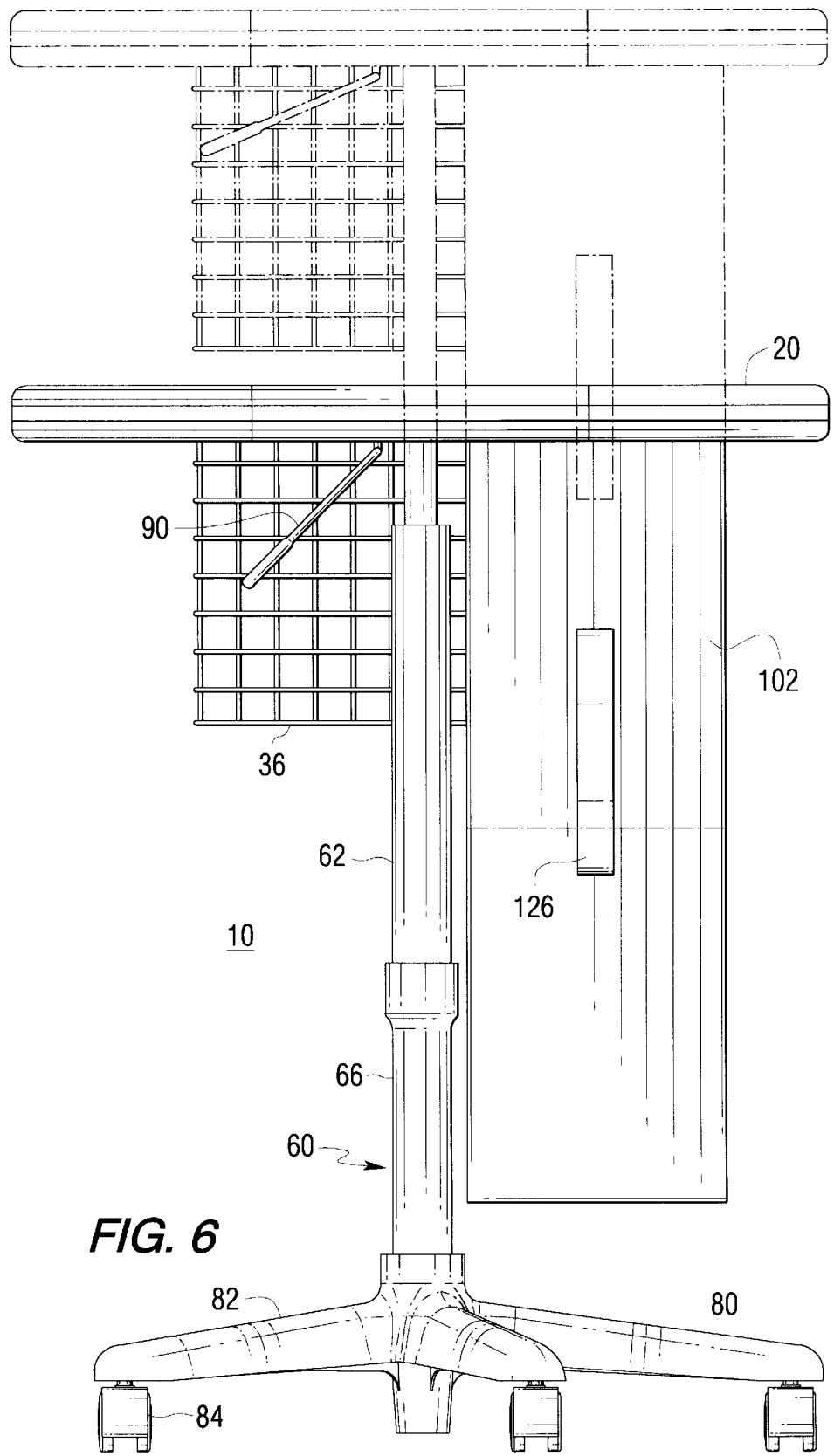
FIG. 6 is a side elevational view of the workstation illustrating the range of positions of the work surface from the lowermost position to the uppermost position shown in phantom.

The height adjustment mechanism of the workstation permits the user to work at either a seated position or a standing position. FIG. 6 illustrates the various height positions of the workstation. The height of the work surface may be adjusted from a height of 28 inches from the floor at the lowermost or seated position where compartment 100 is almost touching the base of the workstation to an uppermost or standing position height of 38 inches from the floor. The power supply which is removably mounted inside the compartment is used to counterbalance the weight of a lap/top computer or other types of equipment that may be carried on the work surface. As the height of the work surface is adjusted from the seated position to the standing position, the power supply counterbalances the weight carried by the work surface and assists in distributing the weight so that a minimum of effort is required to raise or lower the work surface by the user. The power supply in addition to counterbalancing the weight of the equipment carried on the work surface also provides backup power to the equipment carried on the work surface. The power supply may provide up to ten hours of continual use so that the equipment need not be plugged into an electrical receptacle in each room as the user moves from room to room. Therefore, there is no need for separate equipment in each room since that equipment is carried and supported by the workstation. When the workstation is not in use, the electrical cord of the power supply may be plugged into an electrical outlet to recharge the power supply. When the workstation is again needed, the user simply unplugs the electrical cord, winds it around the cleat and proceeds to utilize the equipment without the need for plugging the power supply into an electrical outlet in each room. The cleat prevents the electrical cord from becoming entangled in the base as the workstation is moved from room to room or floor to floor. As the user transports the workstation from room to room, the user may grasp the bottom surface of the work surface which includes the recess or ledge, therefore, providing a finger grip or finger hold for ease of grasping the work surface in order to pull or push the work surface.

Therefore, the invention provides a workstation that is easily portable from room to room or floor to floor in a health care environment. The workstation also includes a height adjustment capability which provides ease of use to workers in a seated position or a standing position. Furthermore, the height adjustment mechanism and the counterbalance means which aids in counterbalancing the weight of the equipment carried on the work surface provide versatility for a user to adjust the position of the work surface from a lower seated position to a higher standing position with minimum effort on the part of the user. This workstation prevents the need for diagnostic equipment or computers to be placed in each room and, therefore, provides a more cost effective and efficient way of providing ease and portability to users.

While certain present preferred embodiments have been shown and described, it is distinctly understood that the invention is not limited thereto but may be otherwise embodied within the scope of the following claims.

We claim:

1. A mobile workstation comprising:

(a) a work surface having a top surface and a bottom surface;

(b) a pedestal for supporting said work surface;

(c) a height adjuster for adjusting the height of said work surface, said height adjuster being housed in said pedestal; and (d) a counterbalance for counterbalancing weight carried by said work surface as the height of said work surface is adjusted, wherein said counterbalance includes a compartment attached to said bottom surface of said work surface, said compartment supporting a ballast for counterbalancing the weight carried by said work surface and including three sides, a top ledge, and a bottom ledge, said top ledge attached to said bottom surface of said work surface by an attachment means including screws.

2. The mobile workstation according to claim 1, where said height adjuster includes a piston and cylinder.

3. The mobile workstation according to claim 1 wherein said ballast includes a power supply for supplying power to electrical equipment which may be carried by said work surface.

4. The mobile workstation according to claim 1 wherein said ballast is removably supported on said bottom ledge of said compartment.

5. The mobile workstation according to claim 1 wherein said pedestal includes a base for supporting said pedestal.

6. The mobile workstation according to claim 5 wherein said base includes casters for providing portability of said workstation.

7. The mobile workstation according to claim 1 wherein said work surface includes at least one basket.

* * * * *